(12) United States Patent
Duerig

(10) Patent No.: US 11,071,620 B2
(45) Date of Patent: Jul. 27, 2021

(54) GRAFT DIMPLING TO IMPROVE CRIMP PROFILE AND REDUCE DELIVERY FORCES

(71) Applicant: Confluent Medical Technologies, Inc., Fremont, CA (US)

(72) Inventor: Thomas Duerig, Fremont, CA (US)

(73) Assignee: Confluent Medical Technologies, Inc., Fremont, CA (US)

( * ) Notice: Subject to any disclaimer, the term of this patent is extended or adjusted under 35 U.S.C. 154(b) by 0 days.

(21) Appl. No.: 15/216,581

(22) Filed: Jul. 21, 2016

(65) Prior Publication Data

US 2017/0020652 A1 Jan. 26, 2017

Related U.S. Application Data

(60) Provisional application No. 62/195,716, filed on Jul. 22, 2015.

(51) Int. Cl.
*A61F 2/07* (2013.01)
*A61F 2/844* (2013.01)
*A61F 2/915* (2013.01)

(52) U.S. Cl.
CPC .............. *A61F 2/07* (2013.01); *A61F 2/844* (2013.01); *A61F 2/915* (2013.01); *A61F 2002/072* (2013.01); *A61F 2002/91533* (2013.01); *A61F 2002/91575* (2013.01); *A61F 2002/91583* (2013.01); *A61F 2210/0057* (2013.01); *A61F 2210/0076* (2013.01); *A61F 2240/00* (2013.01); *A61F 2240/001* (2013.01); *A61F 2250/0036* (2013.01)

(58) Field of Classification Search
CPC .......... A61F 2/07–2002/075; A61F 2250/0036
See application file for complete search history.

(56) References Cited

U.S. PATENT DOCUMENTS

| | | |
|---|---|---|
| 6,077,296 A | 6/2000 | Shokoohi et al. |
| 6,187,036 B1 | 2/2001 | Shaolian et al. |
| 6,197,049 B1 | 3/2001 | Shaolian et al. |
| 6,261,316 B1 | 7/2001 | Shaolian et al. |
| 6,440,161 B1 | 8/2002 | Madrid et al. |
| 6,500,202 B1 | 12/2002 | Shaolian et al. |

(Continued)

FOREIGN PATENT DOCUMENTS

| | | |
|---|---|---|
| EP | 1333787 B1 | 12/2009 |
| WO | WO 99/065419 A1 | 12/1999 |

(Continued)

*Primary Examiner* — Rebecca S Preston
(74) *Attorney, Agent, or Firm* — Shay Glenn LLP

(57) ABSTRACT

A stent-graft assembly is provided for a variety of medical treatments. The stent-graft assembly includes a stent disposed to and attached between an inner layer of graft material and an outer layer of graft material. One of both of the graft layers includes one or more of a depression, dimple or detent that increases the localized surface area of the graft in one or more portions of the stent otherwise susceptible to graft stretching in the absence of the depression, dimple or detent. There is also described a method of forming dimples in selective locations on one or port graft layers in one or more locations relative to a portion of the stent where a portion of the graft may be susceptible to stretching or tearing during crimping or loading operations.

16 Claims, 12 Drawing Sheets

(56) References Cited

U.S. PATENT DOCUMENTS

| | | |
|---|---|---|
| 6,660,030 B2 | 12/2003 | Shaolian et al. |
| 6,733,523 B2 | 5/2004 | Shaolian et al. |
| 6,911,040 B2 | 6/2005 | Johnson et al. |
| 7,520,895 B2 | 4/2009 | Douglas et al. |
| 8,034,100 B2 | 10/2011 | Shaolian et al. |
| 8,062,346 B2 | 11/2011 | Quigley et al. |
| 8,221,494 B2 | 7/2012 | Schreck et al. |
| 8,236,040 B2 | 8/2012 | Mayberry et al. |
| 8,377,110 B2 | 2/2013 | Douglas et al. |
| 8,523,931 B2 | 9/2013 | Mayberry et al. |
| 2001/0056298 A1 | 12/2001 | Brown et al. |
| 2002/0147490 A1 | 10/2002 | Pletzer et al. |
| 2002/0178570 A1 | 12/2002 | Sogard et al. |
| 2005/0222667 A1 | 10/2005 | Hunt |
| 2007/0235899 A1 | 10/2007 | O'Halloran |
| 2007/0250146 A1 * | 10/2007 | Cully ............... A61F 2/07 623/1.2 |
| 2009/0105806 A1 | 4/2009 | Benjamin et al. |
| 2009/0155337 A1 | 6/2009 | Schreck et al. |
| 2010/0131044 A1 | 5/2010 | Patel |
| 2010/0179636 A1 | 7/2010 | Van Pham et al. |
| 2010/0256739 A1 | 10/2010 | Tippett et al. |
| 2010/0261662 A1 | 10/2010 | Schreck et al. |
| 2011/0054586 A1 | 3/2011 | Mayberry et al. |
| 2011/0054587 A1 | 3/2011 | Mayberry et al. |
| 2011/0054594 A1 | 3/2011 | Mayberry et al. |
| 2011/0218617 A1 | 9/2011 | Nguyen et al. |
| 2012/0016456 A1 | 1/2012 | Herbowy et al. |
| 2014/0114434 A1 | 4/2014 | Cottone et al. |
| 2016/0095724 A1 * | 4/2016 | Harris ............... A61F 2/07 623/23.7 |

FOREIGN PATENT DOCUMENTS

| | | |
|---|---|---|
| WO | WO 00/33769 A1 | 6/2000 |
| WO | WO 01/039696 A1 | 6/2001 |
| WO | WO2004/047885 A2 | 6/2004 |
| WO | WO2005/099807 A2 | 10/2005 |
| WO | W2009/055615 A1 | 4/2009 |
| WO | WO2009/064806 A1 | 5/2009 |
| WO | WO2012/139054 A1 | 10/2012 |

* cited by examiner

GRAFT DIMPLING TO IMPROVE CRIMP PROFILE AND REDUCE DELIVERY FORCES

CROSS REFERENCE TO RELATED APPLICATIONS

This application claims priority to U.S. Provisional Patent Application No. 62/195,716, filed Jul. 22, 2015, and titled "GRAFT DIMPLING TO IMPROVE CRIMP PROFILE AND REDUCE DELIVERY FORCES," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

STATEMENT AS TO FEDERALLY SPONSORED RESEARCH

This invention was not made with Government support.

FIELD

This application relates generally to medical devices and particularly to the field of the stent grafts and to techniques for improving crimping, storing and deployment of stent grafts.

BACKGROUND

Stent grafts are commonly constructed by either suturing the tubular graft material to a metallic stent at discrete points, or by bonding the graft to the metallic frame, often encapsulating the frame. In the first case, some motion of the graft is permitted when the stent frame is crimped into its delivery profile. In the second case, however, the bonding is continuous with respect to the metal frame, and the graft must stretch in order to accommodate the crimping operation.

The above problem is depicted in FIG. 1, showing a Teflon encapsulated Nitinol stent, both expanded and crimped into a catheter. As the metallic apecies "scissors" closed, the fabric bunches up in the circumferential direction and stretches in the axial direction. The stretching that the fabric must endure can be gauged by the difference between the cosine of the initial and final strut angles. The stretching of the fabric introduces resistance to the crimping process and contributes to the possibility that the fabric tears.

FIG. 1A illustrates an example of a stent encapsulated and expanded. FIG. 1B is the stent of FIG. 1A as crimped into a catheter. Note the axial stretching in the crimped form. In general, the overall graft get longer during crimping by $(1-\cos(\theta))$ where $\theta$ is the half-angle between neighboring struts in the uncrimped area.

The problem is illustrated in the sketch shown in FIG. 2, illustrating a pair of stent struts joined at an apex at point A, in both the expanded condition and the crimped condition (cross hatched). As one crimps, the struts move as indicated by the arrows. In doing so, point C is brought closer to point B, and point B will be dragged toward point A. If there is no axial constraint of point B relative to point C and point A, the fabric will fold and easily accommodate the radial compression. If one constrains the axial motion of point C relative to point B, however, the struts are unable to move.

The problem illustrated in FIG. 2 can be conveniently demonstrated by taping two rods (chopsticks for example) to a piece of paper in a V-shape to simulate the struts prior to crimping. One notes that the rods can be easily be closed and the paper will fold to accommodate them movement. If, however, one tapes the paper to a table top at points B and C, it will be impossible to close the V-shape without tearing the paper or tape. Even constraining at points C and A will prevent motion.

One can reduce the severity of the problem by selecting graft material that is highly compliant and able to easily stretch (replacing the sheet of paper in the demonstration above with plastic kitchen wrap, for example.) However, such an approach has limited practical benefit in grafts since selection of such a graft material weakens the graft, increasing vulnerability to tearing during delivery, wire crossing, or calcified plaque, as well as bursting due to fluid pressures.

Modifications to the device geometry may also be employed. For example, reducing the apex angle also reduces the severity of the problem as the cosine of the apex angle approaches the unity. This approach can often be undesirable in that it reduces the diametral reduction, unless coupled with a lengthening of the struts. However, lengthening of the struts leads to a reduction in the radial stiffness of the device, which is also highly undesirable. What is needed are improvements to stent grafts in order to reduce or mitigate the aforementioned problems.

SUMMARY OF THE DISCLOSURE

In general, in one embodiment, a stent graft assembly includes a stent structure including a luminal surface, an abluminal surface, a first graft layer, and a second graft layer. The abluminal surface has at least a first radial opening and a second radial opening. Said first and second radial openings extend through said stent structure between said luminal surface and said abluminal surface. Said first and second radial openings are spaced apart along a first direction. The first graft layer has a first thickness disposed along and covering said luminal surface of said stent structure. The second graft layer has a second thickness disposed along and covering a portion of said abluminal surface of said stent structure. One or more dimples formed in the first graft layer and the second graft layer positioned with respect to the stent structure to form a dimple zone of localized additional material.

This and other embodiments can include one or more of the following features. The one or more dimples can be formed so as to from a protrusion in a portion of the graft layer. The one or more dimples can be formed so as to form a protrusion in a portion of the second graft layer. The dimple zone of localized additional material can be selected to accommodate localized stretching of the first and second graft layer when the stent structure is crimped into a stowed configuration.

In general, in one embodiment, a stent graft assembly includes a stent structure having a patterned arrangement of one or more bridges and a graft layer. One or more apexes formed from one or more struts includes a luminal surface and an abluminal surface and has at least a first radial opening and a second radial opening. Said first and second radial openings extend through said stent structure between said luminal surface and said abluminal surface. Said first and second radial openings are spaced apart along a first direction. The graft layer has a thickness disposed along and covering said luminal surface or said abluminal of said stent structure. One or more dimples formed in the graft layer in a pre-selected pattern with respect to the patterned arrangement of one or more bridges and one or more apexes.

This and other embodiments can include one or more of the following features. The one or more dimples can be formed so as to from a protrusion in a portion of the graft layer. The one or more dimples can be formed by interaction of a dimple tool with a surface of the graft such that dimple tool penetrates into less than 50% of the thickness of the graft. The pre-selected pattern can provide localized additional material selected to accommodate localized stretching of the graft layer with respect to the patterned arrangement of one or more bridges and one or more apexes when the stent structure is crimped into a stowed configuration. The pre-selected pattern can provide localized additional material selected to accommodate localized stretching of the graft layer with respect to the patterned arrangement of one or more struts when the stent structure is crimped into a stowed configuration.

In general, in one embodiment, a stent graft assembly includes a stent structure having a patterned arrangement of a plurality of struts arranged into one or more bridges, one or more apexes formed from the plurality of struts including a luminal surface and an abluminal surface and having at least a first radial opening and a second radial opening, and an encapsulating graft layer. Said first and second radial openings extend through said stent structure between said luminal surface and said abluminal surface. Said first and second radial openings are spaced apart along a first direction. The encapsulating graft layer has a thickness disposed along and covering said luminal surface or said abluminal of said stent structure. One or more dimples formed in the encapsulating graft layer in a pre-selected pattern with respect to the stent structure for inducing, providing or enabling folding or deflection of the encapsulating graft material during crimping in those zones of the stent structure having the pre-selected pattern.

This and other embodiments can include one or more of the following features. The encapsulating graft layer can include a first graft layer and a second graft layer.

In general, a method of forming a dimple in a stent graft includes: (1) determining one or more positions on the stent graft where the dimple would improve a subsequent crimping operation; (2) performing a dimple forming operation on the stent graft at the one or more positions; and (3) producing a dimple at the one or more positions.

This and other embodiments can include one or more of the following features. The method can further include warming the stent graft to a temperature above room temperature prior the performing step. The performing step can be conducted using a dimple tool and can include the step of selecting a distal portion shape corresponding to a desired dimple profile. One or both of the stent graft and the dimple tool can be heated to a temperature above room temperature before, or for a period of time after the performing step or the producing step. The method or device can further include one of more steps of (a) performing a general dimpling process to the stent graft or covering material BEFORE applying, affixing or joining the stent graft or covering to the stent; (b) performing a specifically selected dimpling process to the stent graft or covering material BEFORE applying, affixing or joining the stent graft or covering to the stent, whereby the specific selective dimpling is provides the dimples in the pre-selected locations in the graft for the after assembly location of the pre-dimpled region relative to the stent structure and (c) performing one or both of the pre-dimpling methods (a) or (b) and then, after assembly of the stent and graft or covering, perform additional dimpling operations to modify existing dimples or create new dimples, including forming dimples in specific locations based on an inspection of the location of pre-dimpled regions relative to stent components after assembly of the stent and graft or covering material. The depth of one or more dimples formed in a particular stent graft or covered stent can include a dimple formed in a portion of a stent graft or covered stent has a dimple depth in relation to overall stent graft or cover material thickness of no more than 1-5% or 1-10% or 1-20% or 1-30% or 1-40% or 1-50% or 1-60% or 1-70% or 1-80% or 1-90%. A dimple formed in a portion of a stent graft or covered stent has a dimple depth into the graft or cover materials that can be selected so that no portion of the dimple forming tool pierces or perforates or induces a weakness resulting in localized failure in proximity to a dimple or dimple zone. The stent graft adapted and configured for stent grafts or covered stents (including self-deploying or balloon deployed) can be adapted for use in clinical applications such as within bodily lumens including lumens of the venous and arterial vasculature including those of the organs and limbs as well as those stent grafts used in treatment of aortic bifurcation disease; or an endovascular stent graft used to repair fusiform aneurysms or saccular aneurysms/penetrating ulcers of the aorta in the chest; or in peripheral arterial disease management including treatment of atherosclerotic disease, restenotic lesions in the common and/or external iliac arteries, sealing iatrogenic vessel perforations or ruptures, exclusion of aneurysms and pseudoaneurysms; as well as stent grafts used in the treatment of arteriovenous fistulae, and management of failing dialysis grafts such as in an arteriovenous (A-V) access graft, (also known as the venous anastomosis); as well as in an endovascular stent graft indicated to treat stenoses in synthetic arteriovenous bypass grafts; stent grafts and covered stents used for endovascular treatment of infrarenal abdominal aortic or aortoiliac aneurysms (i.e., a so called Aorto-Uni-Iliac or AUI stent) such as those used in patients whose anatomy does not allow for the use of a bifurcated stenting device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 4A:
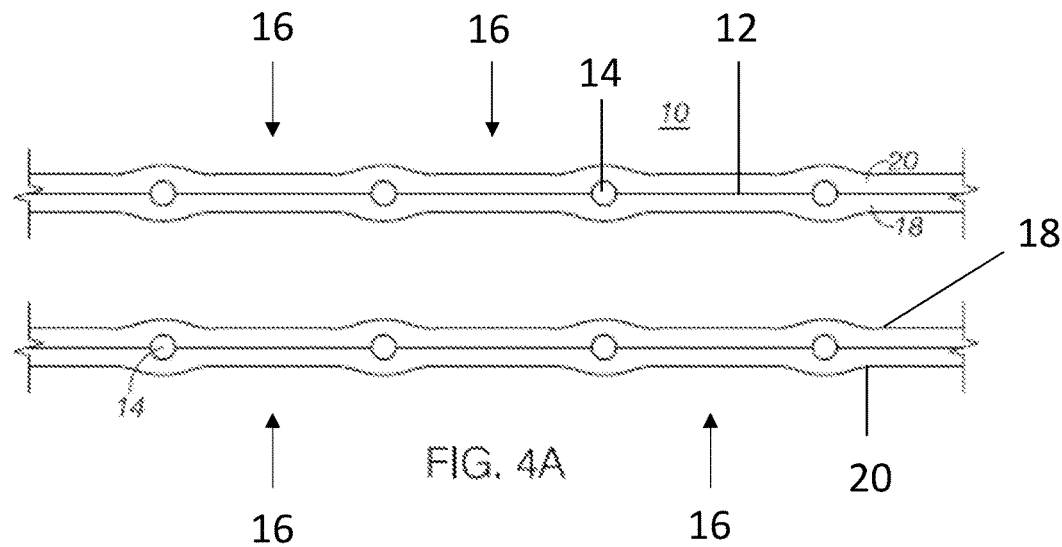
FIGS. 4A and 4B are profile and top views of a stent graft before dimples are applied according to one of more of the various techniques described herein.
Figure 4B:
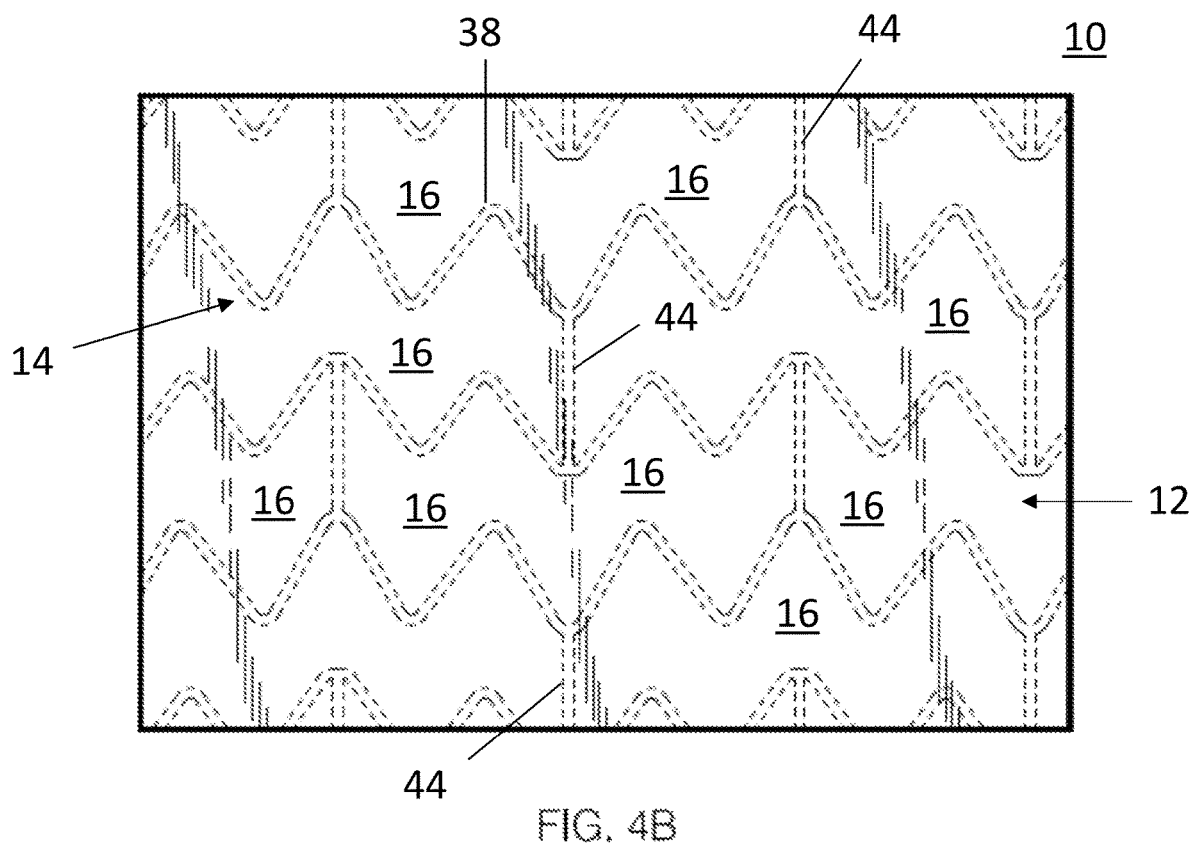

FIGS. 4A and 4B are profile and top views of a stent graft 10 before dimples are applied according to one of more of the various techniques described herein. For purposes of illustration, the stent-graft 10 includes a stent 12 with an inner layer 18 of graft material disposed along the luminal surface of the stent 12 and an outer layer 20 of graft material disposed along the abluminal surfaces of the stent 12. As shown in the figures, it is preferable for the graft layers 18, 20 to cover the entire luminal and abluminal surfaces. However, it is also possible for the graft layers 18, 20 to cover only a portion of the stent 12.

Various types of stents 12 and graft, materials may be used with the inventive dimpling techniques described herein. For example, stents may be made from numerous metals and alloys, including stainless steel, nitinol, cobalt-chrome alloys, amorphous metals, tantalum, platinum, gold and titanium. Stents may also be made from non-metallic materials, such as thermoplastics and other polymers. The structure of the stent may also be formed in a variety of ways to provide a suitable intraluminal support structure. For example, stents may be made from a woven wire structure, a laser-cut cannula, individual interconnected rings, or any other type of stent structure that is known in the art. Regardless of the particular construction of the stent, it is usually desirable for the stem to be flexible in several directions, including both radial and axial flexibility. Stents may also be designed to be either balloon-expandable or self-expandable, depending on the particular application of the stent. Additionally or alternatively, the stein structure may be described as having an patterned arrangement of a plurality of struts 14 arranged into one or more bridges 44, one or more apexes 38 formed from the plurality of struts comprising a luminal surface and an abluminal surface.

In general, most, stents are formed of a support structure having a plurality of radial openings 16 that extend through the structure between the luminal surface of the stent and the abluminal surface of the stent. As shown in the figures, the support structure of the stent 12 may be a pattern of interconnected struts 14. The edges of the struts 14 define a series of open areas 16 that extend radially through the support structure. The arrangement, shape and size of the open areas 16 may vary depending on the geometry of the support structure that is used, and the open areas 16 which are shown are only one example of the many possibilities. Additional details relating to the various locations on the stent and the graft are described below with regard to FIG. 8.

Many different types of graft materials may also be used for different kinds of encapsulation layers or for inner and outer graft layers 18, 20. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues. One graft material that holds particular promise in certain applications is small intestine submucosa (SIS). As those in the art know, SIS material includes growth factors that encourage cell migration within the graft material, which eventually results in the migrated cells replacing the graft material with organized tissues. The graft layers 18, 20 may be formed using a variety of techniques, for example, sheets of graft material may be rolled into tubes with the side edges secured together. Additional details of stent grafts are provided by U.S. Patent Application Publication US 2005/0222667, titled "Stent-Graft with Graft to Graft Attachment," the entirety of which is incorporated herein by reference.

Figures 1A, 1B:
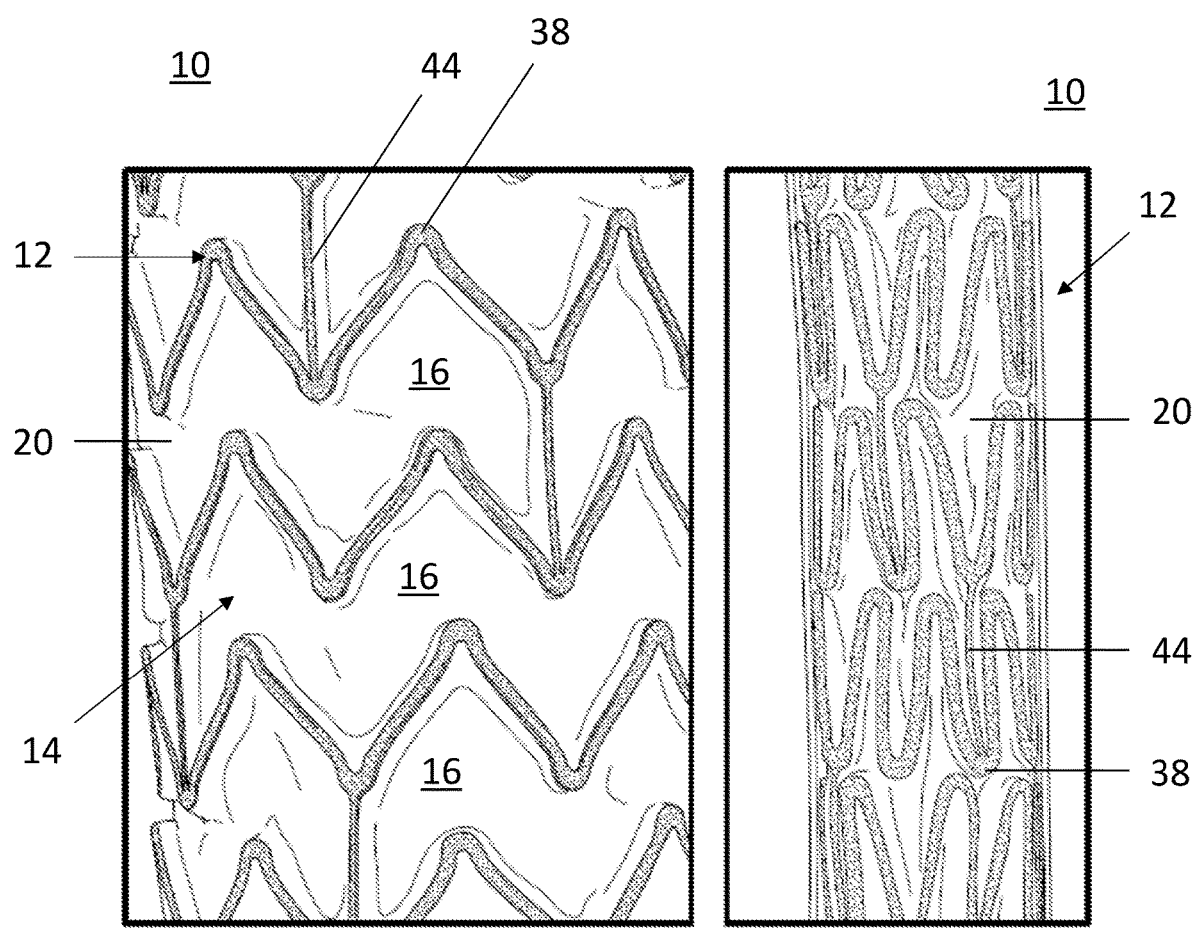
FIG. 1A is an enlarged view of a portion of an expanded encapsulated stent graft.
FIG. 1B is an enlarged portion of the encapsulated stent graft in FIG. 1A in a stowed or crimped condition showing axial stretching of the graft material as a result of the crimping operation.
Figure 2:
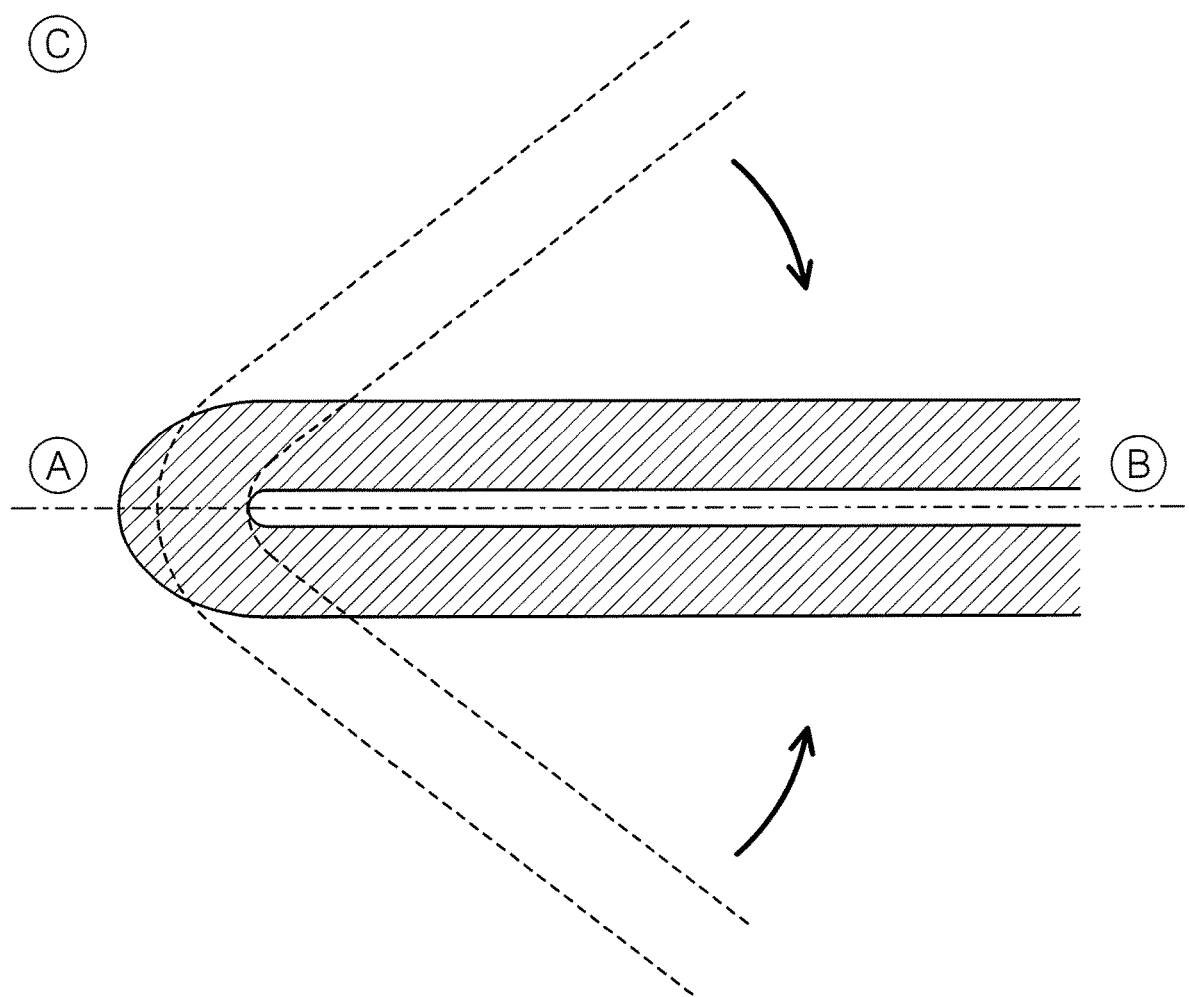
FIG. 2 is a top view of an experimental set up to demonstrate the forces induced onto the graft material.
Figure 3:
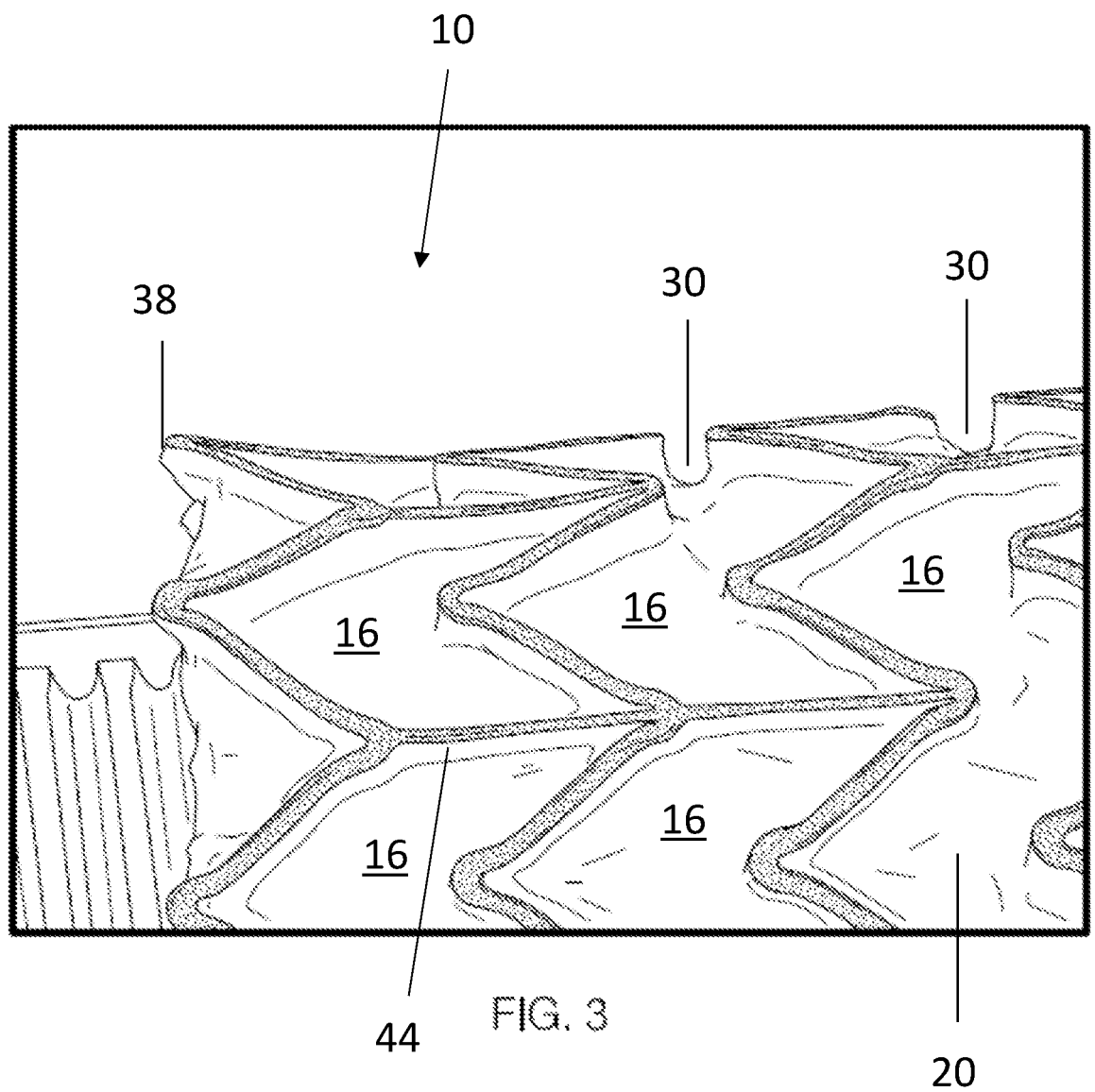
FIG. 3 is a side view of a portion of an embodiment of a stent graft modified according to the inventive technique so as to have two dimples formed in the graft material.

With regard to the present disclosure, we have found that one can overcome the above problem if one dimples the graft, thereby creating extra material in the locations where stretching is anticipated. The extra material provided by, for example, the number, shape, size, and location of a dimple 30 or dimple pattern 45 thus allows the stent graft crimping operation to proceed without having to axially stretch fabric or graft material. An example of graft dimpling is shown in FIG. 3. While the dimples 30 can be made by simply depressing a tool or die onto the graft, it may often be preferred to do so warm, either by preheating the stent graft, and/or by preheating the dimpling tool or die. Such warm dimpling may be necessary to avoid tearing of the fabric and may be adjusted based on the characteristics of a specific graft material. Similarly, creep forming—that is, providing a dwell time to the warm forming operation—may provide further benefits in some additional aspects.

In the various embodiments of the invention, a dimple refers to a localized area of deformity within a selected region or portion of a graft material in a stent graft. A dimple 30 may encompass localized stretch, areas of elongation or even protrusions. The type and number of dimples may be varied by size, shape and amount of graft material deformation, elongation or stretch produced in a given dimple location. Dimples may have a pronounced shape like a protrusion (see FIGS. 5 and 6 for example) or may be a region of localized stretching or deformation without out any particular shape but limited to a specific zone of the stent graft.

In one exemplary method of forming a dimple 30 in a stent graft 10, a dimple tool 40 is used or a dimple process (i.e., stretching of the stent graft) is performed that produces a localized zone of stretched, deformed or elongated graft material. The localized areas may be provided in regular recurring patterns 45 or in isolated locations depending upon the design requirements of a specific stent graft design, materials used and intended application in the anatomy.

In reference to FIG. 3, though difficult to see without stereo vision, the stent fabric has been dimpled, by pressing inward on the critical areas of the fabric using a warmed tool. In various aspects, the exact location and morphology of the dimple may be optimized as well, to allow the needed axial freedom without excessive bulging in the circumferential direction. The exact location and shape of the ideal dimple will depend upon the specific stent design and other factors, but can be determined by finite element analysis. Additionally or alternatively, a stent graft may be forced to undergo the crimping action and then by observation determine where and how the graft material stretches.

Figure 4C:
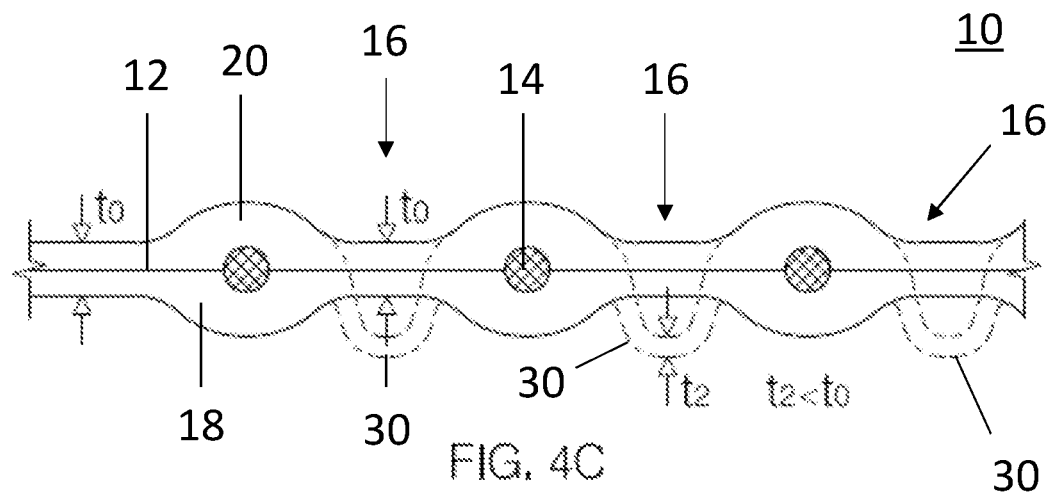
FIGS. 4C and 4D are exemplary profile views of a portion of an encapsulated stent graft having a number of dimples formed by engaging a dimple tool according to an aspect of the inventive method from an outer surface (FIG. 4C) or an inner surface (FIG. 4D).
Figure 4D:
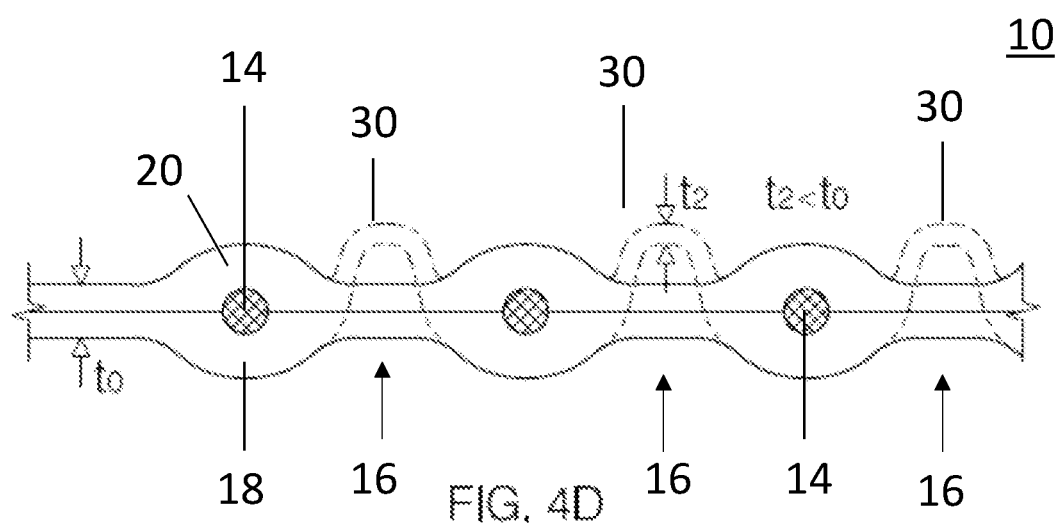

FIGS. 4C and 4D are exemplary profile views of a portion of an encapsulated stent graft having a number of dimples formed by engaging a dimple tool 40 according to an aspect of the inventive method. In FIG. 4C, the dimples 30 (shown in dashed lines) are formed by advancing a dimple tool 40 against the stent graft 10 from an outer surface 20. The original graft thickness $t_0$ is reduced to $t_2$ within the dimple zone 32. In FIG. 4D, the dimples (shown in dashed lines) are formed by advancing a dimple tool against the stent graft 10 from an interior graft surface. The original graft thickness $t_0$ is reduced to $t_2$ within the dimple zone 32.

Figure 5A:
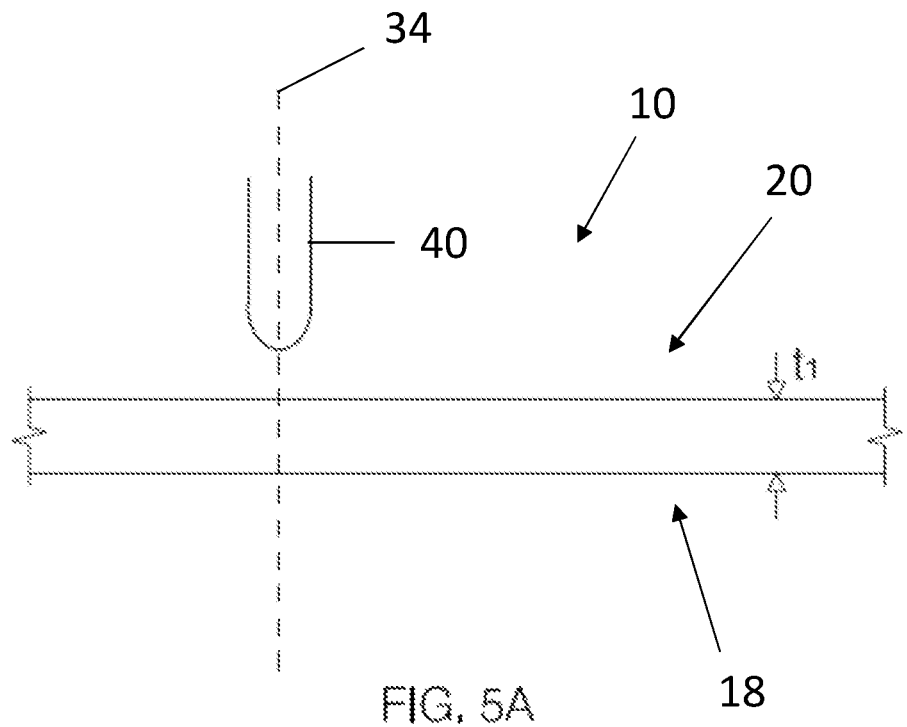
FIG. 5A illustrates a side view dimple tool aligned in a generally vertical or orthogonal dimple formation axis over a portion of a graft having a thickness $t_1$.
Figure 5B:
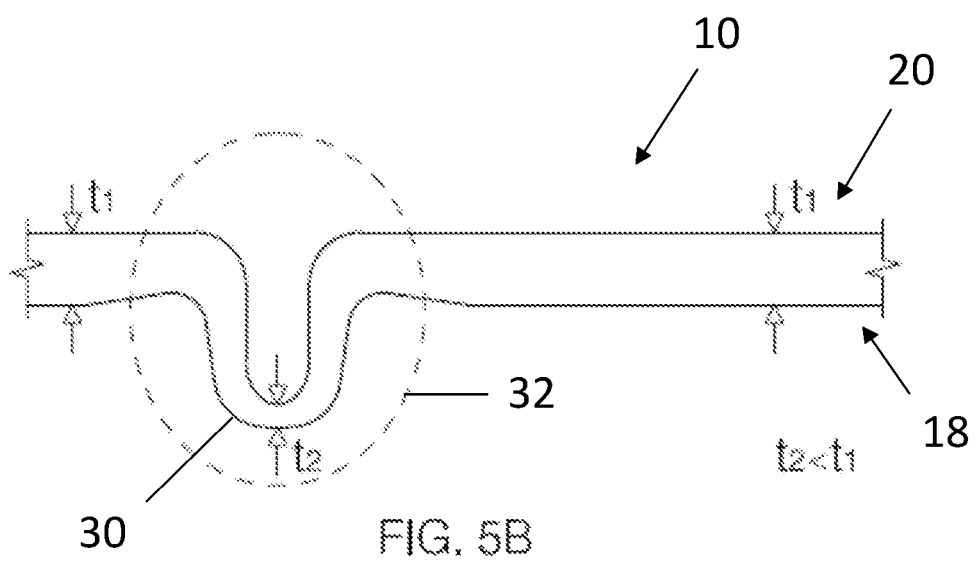
FIG. 5B illustrates a side view of a dimple fruited using the dimple tool and dimple formation axis of FIG. 5A to produce a dimple region in the graft having the dimple profile of the tool in FIG. 5A and a thickness $t_2$, less than the original graft thickness but within mechanical limits for the graft material.

FIG. 5A illustrates a side view dimple tool 40 aligned in a generally vertical or orthogonal dimple formation axis 34 over a portion of a graft having a thickness $t_1$. The dimple tool 40 has a generally cylindrical profile with a rounded tip. FIG. 5B illustrates a side view of a dimple 30 formed using the dimple tool 40 and dimple formation axis of FIG. 5A to produce a dimple region 32 in the graft 10. The dimple has a dimple profile similar to that of the tool in FIG. 5A. Within the dimple region, the graft material is reduced to a thickness $t_2$, less than the original graft thickness $t_1$ but within mechanical limits for the graft material.

Figure 6A:
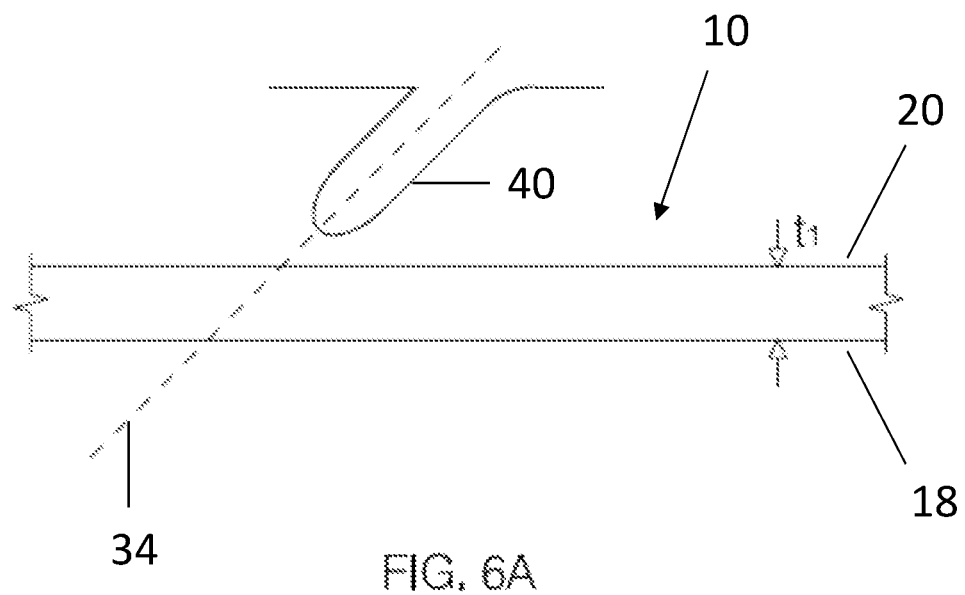
FIG. 6A illustrates a side view of a dimple tool positioned with an inclined dimple formation axis over a portion of a graft having a thickness of $t_1$.
Figure 6B:
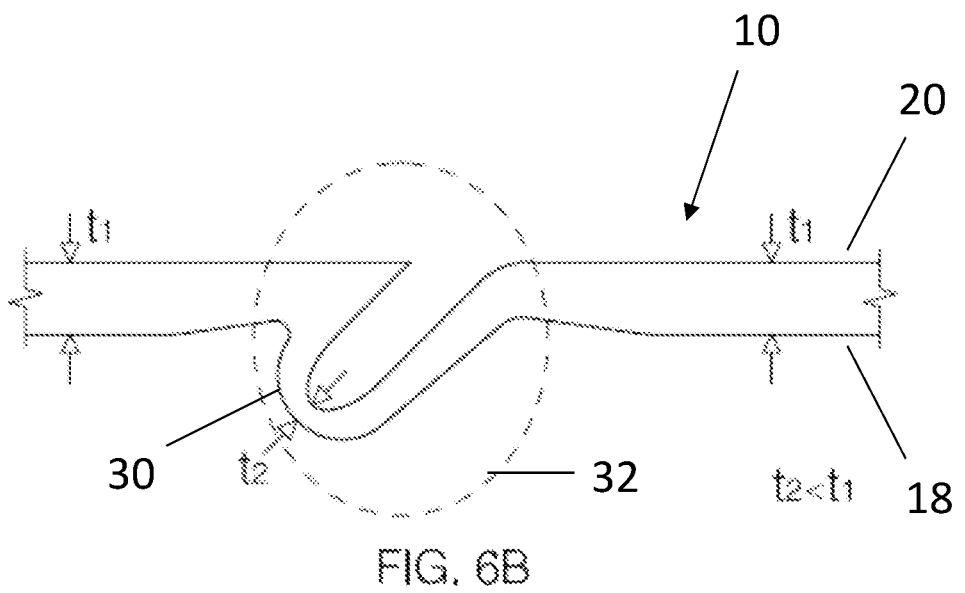
FIG. 6B illustrates a side view of a dimple formed using the dimple tool and dimple formation axis of FIG. 6A to produce a dimple region in the graft having the dimple profile of the tool in FIG. 6A and a thickness $t_2$, less than the original graft thickness but within mechanical limits of the graft material.

FIG. 6A illustrates a side view of a dimple tool positioned with an inclined dimple formation axis over a portion of a graft having a thickness of $t_1$. The dimple tool has a conical or triangular profile and is illustrating an acute dimple formation angle. FIG. 6B illustrates a side view of a dimple formed using the conical, angled dimple tool and dimple formation axis of FIG. 6A. The use of that tool produces a dimple region in the graft having the dimple profile of the tool in FIG. 6A. Within the dimple region, the graft is reduced to a thickness $t_2$, less than the original graft thickness $t_1$ but within mechanical limits of the graft material.

Figure 7A:
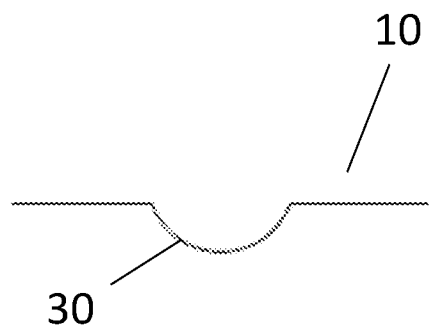
FIG. 7A illustrates an exemplary dimple profile having a semicircular or shallow rounded shape.
Figure 7B:
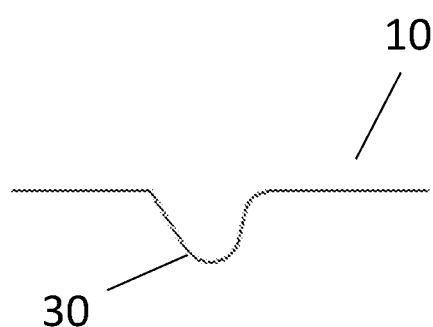
FIG. 7B illustrates an exemplary dimple profile having an oval or elliptical shape.

While FIGS. 5A, 5B, 6A and 6B illustrate two different shapes of dimple forming tools and angles, numerous other dimple shapes and configurations are possible. FIGS. 7A-7F illustrate a number of different exemplary dimple configurations. FIG. 7A illustrates an exemplary dimple profile having a semicircular or shallow rounded shape. FIG. 7B illustrates an exemplary dimple profile having an oval or elliptical shape.

Figure 7C:
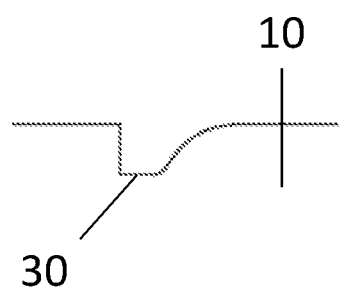
FIG. 7C illustrates an exemplary dimple profile having a compound dimple shape with both a flat portion and a rounded portion.
Figure 7D:
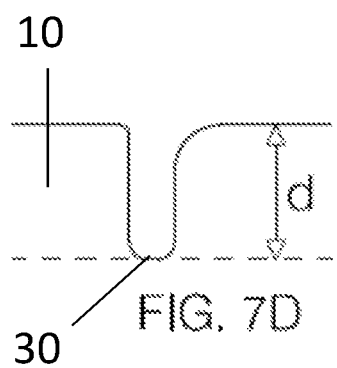
FIG. 7D illustrates another exemplary compound dimple profile having a dimple with an opening, a neck and a bottom.
Figure 7E:
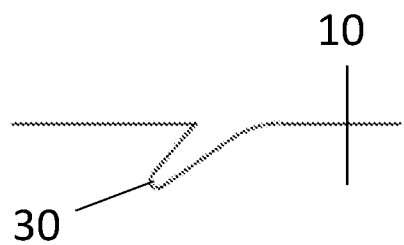
FIG. 7E illustrates an exemplary dimple profile having an inclined dimple formation angle and a dimple profile having a defined tip.
Figure 7F:
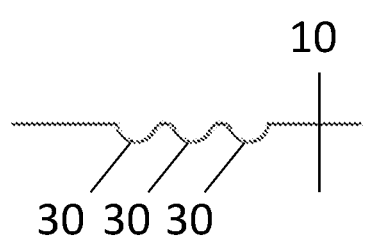
FIG. 7F illustrates an exemplary dimple profile having a series of closely spaced, small or shallow depth dimples.

While the examples so far have been only a single dimple, the dimple tool may be used multiple times in a given region or a dimple tool may include multiple dimple features to form patterns or arrays of dimples. In configurations with multiple dimple tips, the size, shape and angular relationship of the different tips may be the same or different, depending upon the desired dimple characteristics being introduced into a portion of a graft. FIG. 7F illustrates an exemplary dimple profile having a series of closely spaced, small or shallow depth dimples. The closely spaced dimples may, for example, be formed in a single pass by a single dimple tool having multiple tips. Alternatively, a dimple tool with a single tip may be moved in close spacing to form individual close spaced dimples. In addition or optionally, different dimple patterns may be used in different region of a graft based upon the specific graft dimple characteristics desired for the graft-stent interaction in that region. FIG. 7C illustrates an exemplary dimple profile having a compound dimple shape with both a flat portion and a rounded portion.

As appreciated from the above examples, one, more than one or a cluster or an array of dimples may have simple shapes or more complex profiles depending upon the dimple techniques used and the size, shape and orientation of the dimple tool used. For example, FIG. 7D illustrates another exemplary compound dimple profile having a dimple with an opening, a neck and a bottom. In contrast to the shape, size and angle illustrated in FIG. 6B, FIG. 7E illustrates an exemplary dimple profile having an inclined dimple formation angle and a dimple profile having a defined tip.

Figure 8:
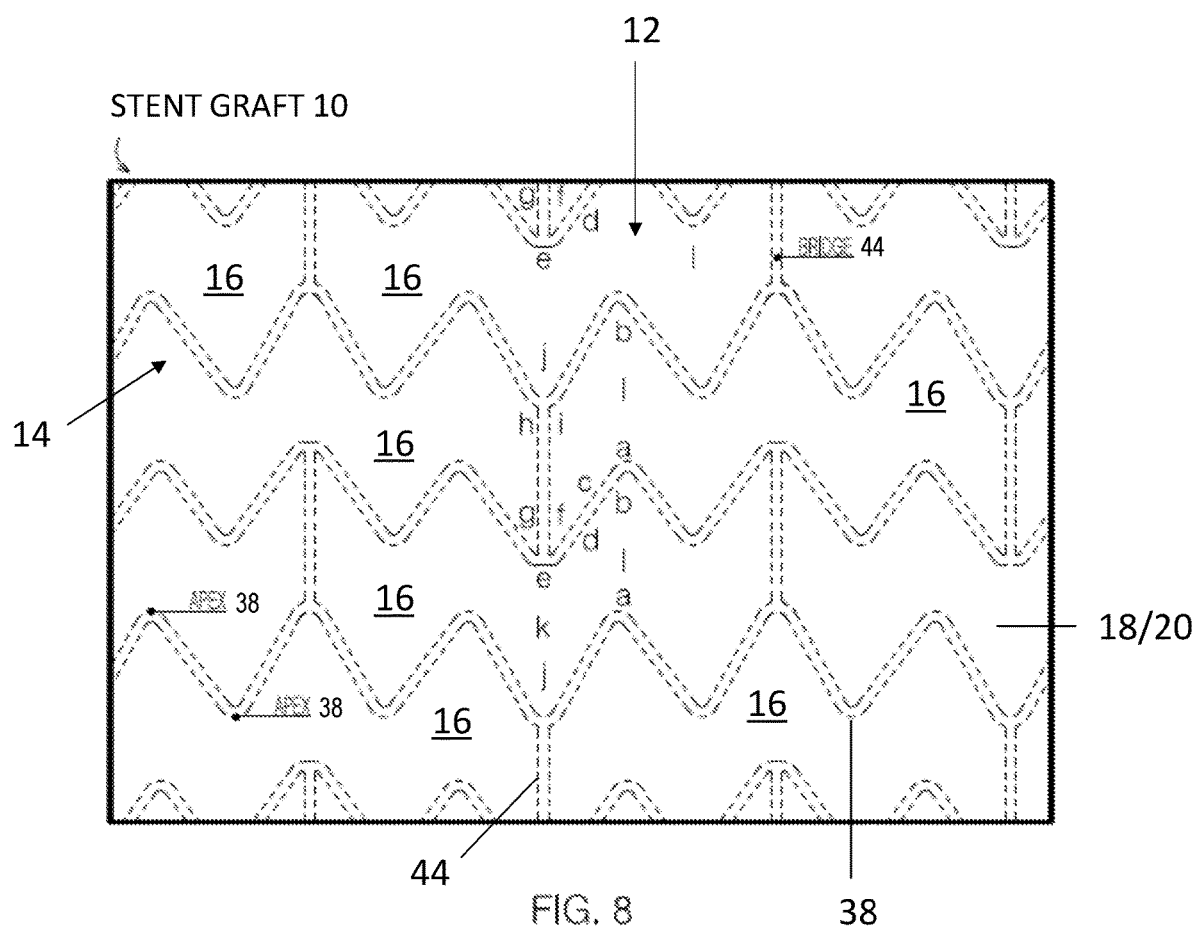
FIG. 8 is a top view of a number of illustrative dimple locations in an exemplary stent graft according to the inventive techniques.

FIG. 8 is a top view of a number of possible dimple locations in an illustrative stent graft according to the inventive techniques.

Stent graft position definitions—defined by location
a: distal to free apex (i.e., not joined to a bridge element)
b: proximal to free apex (i.e., not joined to a bridge element)
c: adjacent to a distal portion of a strut between a free apex and an apex joined to a bridge element
d: adjacent to a proximal portion of a strut between a free apex and a free side of an apex joined to a bridge element
e: adjacent to a proximal portion of the free side of an apex joined to a bridge element
f and g: adjacent to a joined apex having a distally extending strut
h and i: adjacent to a joined apex having a proximally extending strut
j: adjacent to a distal portion of the free side of an apex joined to a bridge element
k: between and adjacent to positions e and j
l: between and adjacent to positions a and b A single dimple or more than one dimple may be formed at a position within a stent graft location. A dimple forming tool may be adapted and configured to form one or more than one dimple at a dimple position. Additionally or alternatively, a dimple forming tool may be adapted and configured to simultaneously form a dimple pattern or array where multiple dimples are formed each one in a different stent graft location. In one aspect, a dimple forming tool may be adapted and configured to simultaneously form all dimples along an axial position of a stent graft. The axial dimple array for a particular stent graft may then be formed by engaging the stent graft and the axial dimple tool, disengaging the tool and then indexing the stent graft and then engaging the axial dimple tool to form the next axial dimple array. In another aspect, a dimple forming tool may be adapted and configured to simultaneously form all dimples along a radial or a circumferential position of a stent graft, or the entire graft at one time. The circumferential or radial dimple array for a particular stent graft may then be formed by engaging the stent graft and the radial or circumferential dimple tool, disengaging the tool and then indexing the stent graft and then engaging the radial or circumferential dimple tool to form the next radial or circumferential dimple array. In still another variation, there is an entire stent graft dimple array wherein the dimple tools are arranged in a structure sized and shaped to receive the stent graft. The stent graft is then fixed in position relative to the dimple array device. Thereafter dimple forming tools are then advanced in the desired positions to form the dimples in the desired position. A dimple forming device may be made specifically for a particular stent graft configuration or stent graft size.

One or more dimple is the placed at a position relative to a stent graft location. Dimples may be arranged in a variety of patterns including one or more different dimple shapes (see FIGS. 7A-7F).

Figure 9:
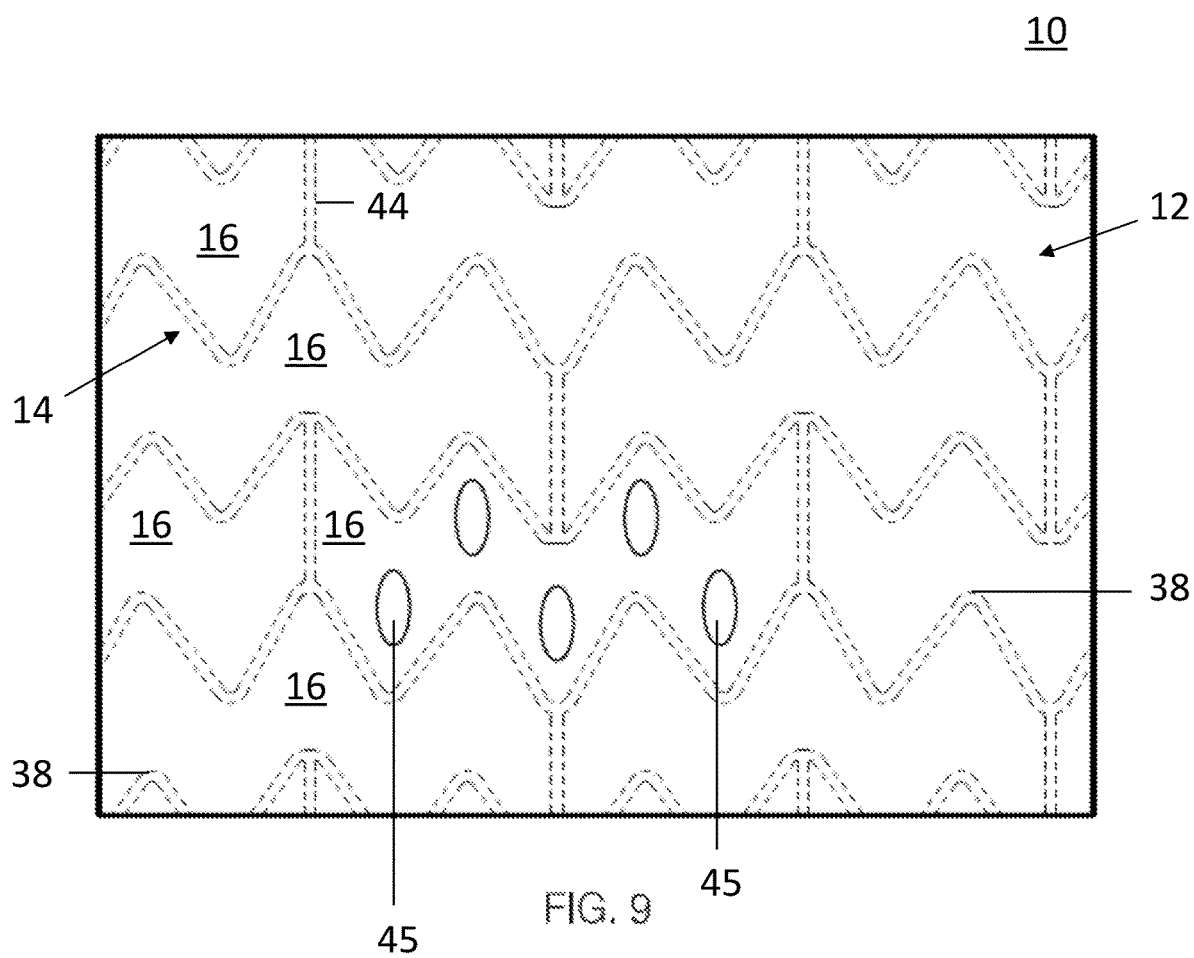
FIG. 9 is a top view of a first exemplary dimple location pattern in a stent graft according to an aspect of the inventive technique.

FIG. 9 is a top view of an exemplary dimple location patterns 45 in a stent graft 10 according to an aspect of the inventive technique. In this illustrative embodiment there are dimples 30 located between adjacent struts 14. Using the positions detailed in FIG. 8 these dimples 30 are formed to cover three positions. Dimples 30 are shown in positions near locations b, 1 and a and also near locations e, k and j. While shown in only one region of the graft, it is to be appreciated that the dimple pattern 45 at a location may be repeated across all or a portion of the stent. In this illustrative embodiment, the dimple patterns align generally with the longitudinal axis of the stent graft.

Figure 10:
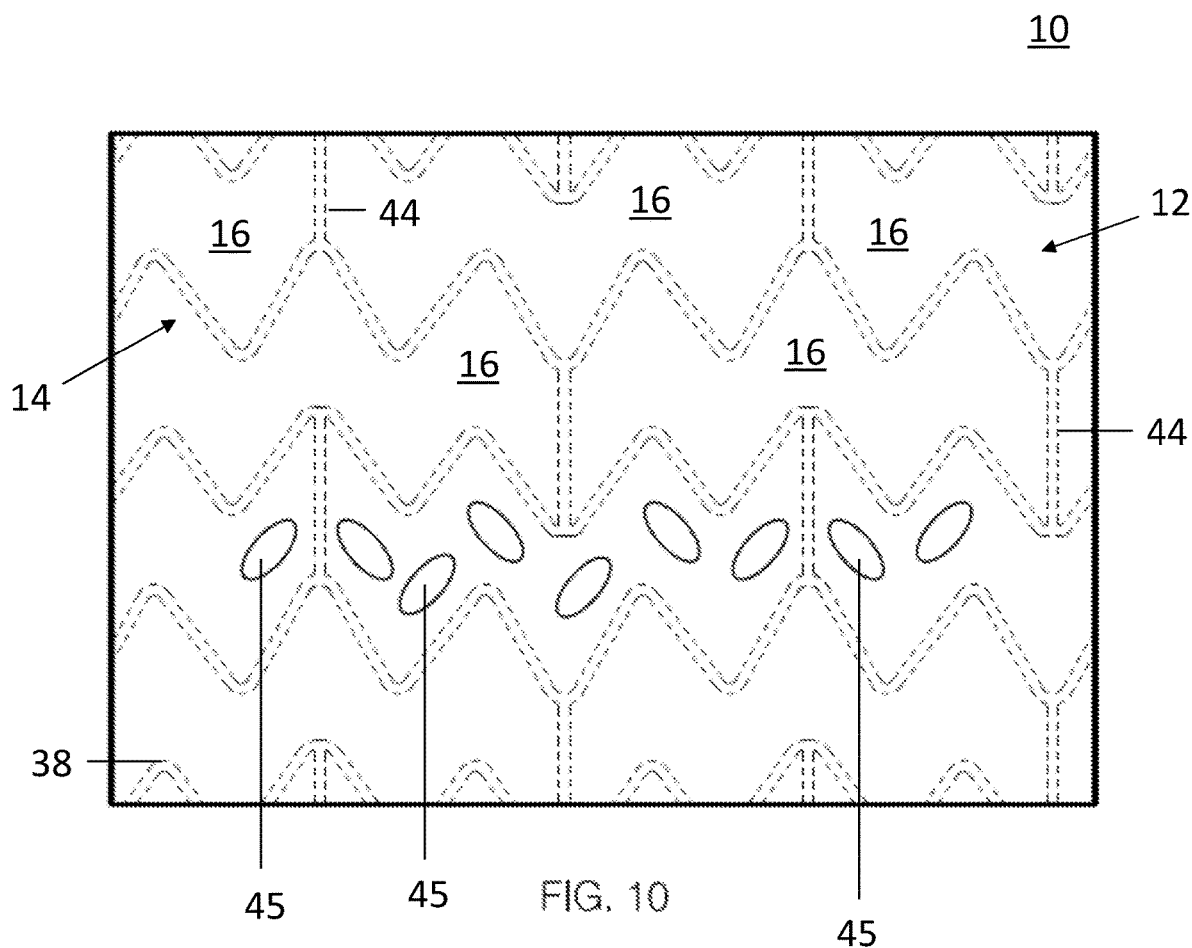
FIG. 10 is a top view of a second exemplary dimple location pattern in a stent graft according to another aspect of the inventive techniques.

FIG. 10 is a top view of another exemplary dimple location pattern 45 in a stent graft 10 according to another aspect of the inventive techniques. In this illustrative embodiment there are dimples 30 located between adjacent struts 14. Using the positions detailed in FIG. 8 these dimples are formed to cover two positions. Dimples are shown in positions near locations i and l and also near k and l. While shown in only one region of the graft, it is to be appreciated that the dimple pattern 45 at a location may be repeated across all or a portion of the stent. In this illustrative embodiment, the dimple patterns 45 align generally with the angled portions of the stent pattern. In contrast to FIG. 9, the dimple pattern 45 in this embodiment is angled relative to the longitudinal axis of the stent graft.

Figure 11:
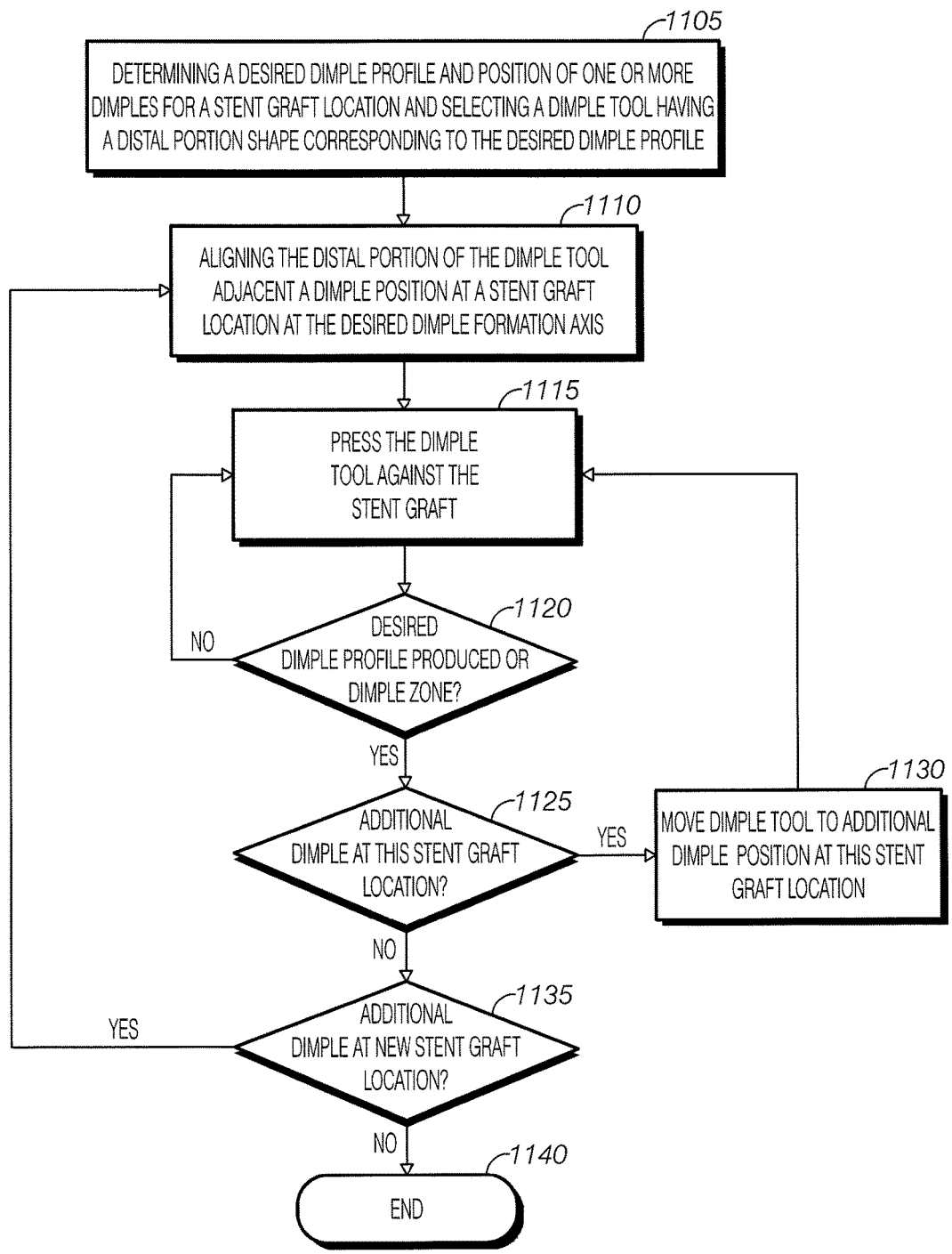
FIG. 11 is a flow chart of an exemplary method of forming dimples in a graft.

FIG. 11 is a flow chart of an exemplary method 1100 of forming dimples in a graft.

First, at step 1105, there is a process of determining a desired dimple profile and position of one or more dimples for a stent graft location and selecting a dimple tool having a desired distal portion shape corresponding to the desired dimple profile.

Next, at step 1110, there is a process of aligning the distal portion of the dimple tool adjacent to a dimple position at a stent graft location at the desired dimple formation axis.

Next, at step 1115, the dimple tool is pressed into contact with the graft.

Next, determine if the desired dimple profile is produced or dimple zone is produced? (step 1120). If the answer is "No" then return to step 1115 and continue to press the dimple tool against the graft. If the answer is "Yes" then proceed to step 1125. At step 1125, determine if additional dimples are to be formed at this dimple location? If the answer to step 1125 is "Yes" then proceed to step 1130 and position the dimple tool to the additional dimple location. If the answer to step 1125 is "No" then proceed to step 1135.

At step 1135 determine if additional dimples are to be formed at a different stent graft location. If the answer is "Yes" then proceed to step 1110 and repeat the above steps for additional dimple formation. If the answer is "No" and all dimples for this graft have been formed, then proceed to step 1140 where the method ends.

Additionally or optionally, the method of forming dimples in a portion of a stent graft may optionally include operations conducted on the stent graft that result in stretching, twisting or combinations thereof. In one specific embodiment, the dimple forming operation is performed on a stent graft that has been heated to a temperature above room temperature or to a temperature selected based on the type of material or other characteristics of the stent graft to further the benefits of dimple formation. In still other embodiments, operations are performed to place the stent graft under tension alone or in combination with torsion in order to provide an overall degree of slackness sufficient to improve the crimping process as described herein. In another aspect, prior to crimping a stent graft, the entire stent graft assembly is pulled so as to sufficiently plastically stretch the graft sufficient to improve a subsequent crimping process. In any of the above embodiments, the stent graft may be warmed to a temperature above room temperature and within a range to assist in the desired plastic deformation.

The advantages of the several embodiments of present invention may be applied to any of a wide variety of stent grafts. Patterns and combinations of dimples illustrated and described in FIGS. 5-8 through 8 may be applied in various combinations of stent grafts including stents made from nitinol, stainless steel and nitinol and other alloys thereof, as well as the various materials listed in Appendix A. Similarly, graft material may be open, single layer, 2 or more layers made from any suitable material such as for example, expandable polytetrafluoroethylene (ePTFE), polytetrafluoroethylene (PTFE), Dacron, polyester, fabrics, collagen and as well as synthetic polymers and natural tissues.

In still other aspects, the inventive techniques described herein to introduce one or more dimples into the graft material in selected positions in relation to the associated stent structures, provides or enables preferential folding or deflection of the graft material in those zones during crimping. In this way, the graft material is better able to deflect or fold as the stent undergoes crimping induced geometry changes. As a result, the techniques described herein may be modified given the thickness of a particular stent graft or covered stent materials. In various different embodiments, one or more of these additional alternative techniques may be employed such as: (a) performing a general dimpling process to the stent graft or covering material before applying, affixing or joining the stent graft or covering to the stent; (b) performing a specifically selected dimpling process to the stent graft or covering material before applying, affixing or joining the stent graft or covering to the stent, whereby the specific selective dimpling is provides the dimples in the pre-selected locations in the graft for the after assembly location of the pre-dimpled region relative to the stent structure and (c) performing one or both of the pre-dimpling methods (a) or (b) and then, after assembly of the stent and graft or covering, perform additional dimpling operations to modify existing dimples or create new dimples, including forming dimples in specific locations based on an inspection of the location of pre-dimpled regions relative to stent components after assembly of the stent and graft or covering material.

In still other aspects, the depth of one or more dimples formed in a particular stent graft or covered stent depends on a number of factors including the physical characteristics of the graft or covering material in use. Of particular importance is the relationship between the dimple depth and profile in relation to the overall thickness of the graft or covering material in the region of dimpling. It is to be appreciated that many of the dimple embodiments are shown enlarged or not to scale in order to show exemplary locations of the dimples and for clarity of explanation. In some embodiments a dimple formed in a portion of a stent graft or covered stent has a dimple depth in relation to overall stent graft or cover material thickness of no more than 1-5% or 1-10% or 1-20% or 1-30% or 1-40% or 1-50% or 1-60% or 1-70% or 1-80% or 1-90%.

Alternatively, some embodiments a dimple formed in a portion of a stent graft or covered stent has a dimple depth into the graft or cover materials that is selected so that no portion of the dimple forming tool pierces or perforates or induces a weakness resulting in localized failure in proximity to a dimple or dimple zone. In some other embodiments, a stent graft or covering material has a thickness of between about 75 microns to 300 microns or other thicknesses depending upon clinical application of the stent graft.

EXAMPLE

A stent graft having a thickness 100 microns has been modified to have one or more dimples formed in the graft material with a depth of less than 75 microns, less than 50 microns or less than 20 microns.

In still further aspects, the dimple induced graft folding zones and dimpling patterns and methods described herein may be provided with advantage to a number of different types of covered stents or stent grafts, in a number of different clinical and anatomical applications including by way of example and not limitation: stent grafts or covered stents (including self-deploying or balloon deployed) are adapted for use in clinical applications such as within bodily lumens including lumens of the venous and arterial vasculature including those of the organs and limbs as well as those stent grafts used in treatment of aortic bifurcation disease; or an endovascular stent graft used to repair fusiform aneurysms or saccular aneurysms/penetrating ulcers of the aorta in the chest; or in peripheral arterial disease management including treatment of atherosclerotic disease, restenotic lesions in the common and/or external iliac arteries, sealing iatrogenic vessel perforations or ruptures, exclusion of aneurysms and pseudoaneurysms; as well as stent grafts used in the treatment of arteriovenous fistulae, and management of failing dialysis grafts such as in an arteriovenous (A-V) access graft, (also known as the venous anastomosis); as well as in an endovascular stent graft indicated to treat stenoses in synthetic arteriovenous bypass grafts; stent grafts and covered stents used for endovascular treatment of infrarenal abdominal aortic or aortoiliac aneurysms (i.e., a so called Aorto-Uni-Iliac or AUI stent) such as those used in patients whose anatomy does not allow for the use of a bifurcated stenting device.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A stent graft assembly, comprising:
   a stent structure comprising a luminal surface and an abluminal surface and having at least a first radial opening and a second radial opening, said first and second radial openings extending through said stent structure between said luminal surface and said abluminal surface, wherein said first and second radial openings are spaced apart along a first direction;
   a first graft layer having a first thickness disposed along and covering said luminal surface of said stent structure;
   a second graft layer having a second thickness disposed along and covering a portion of said abluminal surface of said stent structure; and
   one or more dimples formed in the first graft layer and the second graft layer of localized plastically deformed material within radial openings along the first direction, and within the localized plastically deformed material a thickness of the first graft layer is less than the first thickness and a thickness of the second graft layer is less than the second thickness.

2. The stent graft assembly of claim 1 wherein the one or more dimples are formed so as to from a protrusion in a portion of the first graft layer.

3. The stent graft assembly of claim 1 wherein the one or more dimples are formed so as to form a protrusion in a portion of the second graft layer.

4. The stent graft assembly of claim 1 wherein the localized plastically deformed material is positioned relative to the radial openings to accommodate localized stretching of the first and second graft layer when the stent structure is crimped into a stowed configuration.

5. The device of claim 1 wherein the stent graft assembly is adapted and configured for use in clinical applications within lumens of the venous and arterial vasculature including those of the organs and limbs.

6. The device of claim 1 wherein a depth of the one or more dimples is less than 75 microns.

7. The device of claim 1 wherein the first direction is along a longitudinal axis of the stent structure.

8. The device of claim 1 wherein the first direction is along an angled portion of a stent pattern in the stent structure.

9. A stent graft assembly, comprising:
   a stent structure having a patterned arrangement of one or more bridges, one or more apexes formed from one or more struts the stent structure having a luminal surface and an abluminal surface and having at least a first radial opening and a second radial opening, said first and second radial openings extending through said stent structure between said luminal surface and said abluminal surface, wherein said first and second radial openings are spaced apart along a first direction;
   a graft layer having a thickness disposed along and covering said luminal surface or said abluminal surface of said stent structure; and
   one or more dimples formed in the graft layer within the first radial opening and the second radial opening in a pre-selected pattern providing preferential stretching of the graft layer with respect to the patterned arrangement of one or more bridges and one or more apexes, and a thickness of the graft layer where the one or more dimples are formed is less than the graft layer thickness.

10. The stent graft assembly of claim 9 wherein the one or more dimples are formed so as to form a protrusion in a portion of the graft layer.

11. The stent graft assembly of claim 9 wherein the one or more dimples extend from the luminal surface or the abluminal surface of the graft into less than 50% of the thickness of the graft.

12. The stent graft assembly of claim 9 wherein the pre-selected pattern provides localized additional material selected to accommodate localized stretching of the graft layer with respect to the patterned arrangement of one or more bridges and one or more apexes when the stent structure is crimped into a stowed configuration.

13. The stent graft assembly of claim 9 wherein the pre-selected pattern provides localized additional material selected to accommodate localized stretching of the graft layer with respect to the patterned arrangement of one or more struts when the stent structure is crimped into a stowed configuration.

14. The device of claim 9 wherein the one or more dimples formed in a portion of the graft layer has a dimple depth into the graft layer that is selected so that no portion of the dimple forming tool pierces or perforates or induces a weakness resulting in localized failure in proximity to a dimple or dimple zone.

15. A stent graft assembly, comprising:
a stent structure having an patterned arrangement of a plurality of struts arranged into one or more bridges, one or more apexes formed from the plurality of struts the stent structure having a luminal surface and an abluminal surface and having at least a first radial opening and a second radial opening, said first and second radial openings extending through said stent structure between said luminal surface and said abluminal surface, wherein said first and second radial openings are spaced apart along a first direction;
an encapsulating graft layer having a thickness disposed along and covering said luminal surface or said abluminal surface of said stent structure; and
one or more dimples formed in the encapsulating graft layer surrounded by radial openings in a pre-selected pattern of plastic deformation within the graft layer with respect to the stent structure for inducing, providing or enabling folding or deflection of the encapsulating graft material during crimping in those zones of the stent structure having the pre-selected pattern, and a thickness of the graft layer having the one or more dimples is less than the thickness of the encapsulating graft layer.

16. A stent graft assembly of claim 15 the encapsulating graft layer comprising a first graft layer and a second graft layer.

\* \* \* \* \*